United States Patent [19]

Potini

[11] Patent Number: 4,944,938

[45] Date of Patent: Jul. 31, 1990

[54] ANTIPERSPIRANT AND DEODORANT

[75] Inventor: A. Chimpirama Potini, Somerset, N.J.

[73] Assignee: Colgate-Palmolive Company, New York, N.Y.

[21] Appl. No.: 285,100

[22] Filed: Dec. 16, 1988

[51] Int. Cl.$^5$ .................. A61K 7/32; A61K 7/34; A61K 7/38

[52] U.S. Cl. .................. 424/68; 424/65; 424/66

[58] Field of Search .................. 424/65, 66, 68

[56] References Cited

U.S. PATENT DOCUMENTS

| | | | |
|---|---|---|---|
| 2,814,584 | 11/1957 | Daley | 424/68 |
| 4,053,581 | 10/1977 | Pader et al. | 424/68 |
| 4,065,564 | 12/1977 | Miles, Jr. et al. | 424/68 |
| 4,073,880 | 2/1978 | Pader et al. | 424/68 |
| 4,151,272 | 4/1979 | Geary et al. | 424/68 |
| 4,154,816 | 5/1979 | Roehl et al. | 424/68 |
| 4,264,586 | 4/1981 | Callingham | 424/68 |
| 4,265,878 | 5/1981 | Keil | 424/68 |
| 4,346,079 | 8/1982 | Roehl | 424/68 |
| 4,383,988 | 5/1983 | Teng et al. | 424/68 |
| 4,435,382 | 3/1984 | Shin et al. | 424/66 |
| 4,499,069 | 2/1985 | Krafton | 424/66 |
| 4,673,570 | 6/1987 | Soldati | 424/66 |

OTHER PUBLICATIONS

Fox, Cosmetic & Toiletries, 11/1984, vol. 99, pp. 19 to 25, 36, 38, 40, 42, 44, 47, 48 and 50.
Geria, Cosmetics & Toiletries, 11/1984, vol. 99, pp. 55, 56, 58, 60, 62, 64, 65, 66.

Primary Examiner—Dale R. Ore
Attorney, Agent, or Firm—Robert Sullivan; Murray Grill; Richard Ancel

[57] ABSTRACT

A clear quick drying highly active antiperspirant and deodorant gel free of monohydric alcohols comprising an antiperspirant, a volatile water soluble emollient, volatile siloxanes a, a volatile water insoluble emollient, a coupling agent and a solubilizer.

4 Claims, No Drawings

ANTIPERSPIRANT AND DEODORANT

BACKGROUND OF THE INVENTION

Cosmetic deodorants are preparations which mask remove or decrease perspiration odors, or performs all of these functions.

In order to control objectable odors of perspiration it is necessary to check the flow of excess perspiration or to eliminate or mask the odor or both.

Although variety of substance which have astrigent action inhibit the flow of perspiration, the mechanism of operation of antiperspirants is not clearly defined.

The aluminum compound that is mostly widely used in antiperspirant compositions is the aluminumchlorohydroxide complex commonly referred to as aluminumchlorohydrate or aluminumchlorohydroxide. The product is a 5/6 basic aluminumchloride complex with the atomic ratio of aluminum to chloride of 2:1. It is glass like rather than crystalline in the dry form and is readily soluble in water. At 20% solution aluminumchlorhydrate has a pH of approximately 4.2 and has good buffering capacity. The aluminumchlorhydrate is non irrating or sensitising to normal skin and does not damage fabrics. The aluminumchlohydrate complex is sold under a variety of tradenames. It is sold in dry, regular or powdered form or as a 50% solution.

U.S. Pat. No. 4,673,570 to Soldati describes a uniform clear gelled antiperspirant composition free of waxes and additional gelling agents.

U.S. Pat. No. 4,435,382 to Shin et al describes a anhydrous alcoholic antiperspirant suspension containing aluminum or aluminum-zirconium salt complexes.

U.S. Pat. No. 4,383,988 to Teng et al describes a clear viscous gelled antiperspirant composition consisting of a gelled solution of a alcohol solvent and a gelling agent for the solvent.

U.S. Pat. Nos. 4,053,581 and 4,073,880 to Pader et al describe antiperspirant formulations containing siloxanes.

U.S. Pat. No. 4,154,816 to Roehl et al describes a solid antiperspirant composition that contains a trihydric alcohol, a gelling agent and an amide.

BROAD DESCRIPTION OF THE INVENTION

The instant invention relates to a clear non-alcoholic, quick drying, highly active, antiperspirant and deodorant gel. The gel is stable both at room temperatures and at higher temperatures, it is nonstinging and leaves no white residue on the skin. The formulation does not stain clothes. The antiperspirant deodorant gel does not include gelling agents, waxes or clays. Unlike other gels it is very low in water content and yet is a quick drying composition. The formulation does not contain low boiling monohydric alcohols.

The antipersprant gel instant invention is an improvement over the gels of the prior art which are unaesthetic, slow drying and retain a high degree of tackiness because of the high water content in the high concentration of emulsifying agents. Most of the clear gel antiperspirants of the prior art turn opaque when exposed to air. In contrast the gel of the instant invention remains clear and non-greasy.

The gel of the instant invention does not include monohydric alcohols having 2 to 8 carbon atoms. One of the essential features of the gel of the instant application is the use of 3 to 5 carbon atom trihydric alcohols as coupling agents. These polyhydric alcohols act as solubulizers in the system and keep the system very stable and clear.

DETAILED DESCRIPTION OF THE INVENTION

The antipersperant in the formulations of the instant invention is aluminumchlorhydrate. The aluminumchlorhydrate available under the tradename of Wickenol CPS 331 gives satsifactory results the aluminumchlorhydrate commercially available under the tradename Rehydrol II can also be used. This aluminumchlorhydrate is more water soluble than the Wickenol CPS 331.

The aluminumchlorhydrate is present in about 18–26% by weight of the formulation, preferably about 22–26% by weight.

A second essential ingredient of the formulation is the volatile water insoluble emollient. The preferred water insoluble emollient is isostearylbenzoate. The isostearylbenzoate available under the tradename of Finsolv-SB is preferred. This water insoluble emollient is a good fragrance fixative and extender, does not leave a dry feel and gives the skin a somewhat softer velvety feel.

The isostearylbenzoate is present as about 13–20% of the formulation preferably about 13–15% of the formulation.

The formulation also contains a soluble emollient the preferred soluble emollient is cetylether more specifically the cethylethers available under the tradenames PPG-10, Procetyl 10. This emollient is soluble in hydroalcohol systems. The cethylether is also an excellent coupling agent for incorporation of oils into the hydrosystem and can couple perfume oils well into the emollients. Another cethylether in the product available under the tradename PPG-5 Ceteth-20, procetol AWS. This compound is soluble in water, a good emollient as well as dispersing agent. Another volatile emollient is polyoxypropylene(15) stearylether available tradename of ARLAMOL E.

The emollients are present as about 14–25% by weight of the formulation preferably above 20–25% by weight of the formulation. A mixture of the PPG-10 and PPG-5 compounds is the preferred emollient.

The formulation also contains solubilizers such as propylene glycol and glycerine. These solubilizers are present at about 2–6% by weight of the formulation preferably 3–4% by weight.

The formulation also contains volatile siloxanes. The preferred volatile siloxanes are low molecular weight polydimethylcyclosiloxanes. These siloxanes are available under variety of tradenames. The compositions designated Silicone 244, 334 and 556 by Dow Corning give satisfactory results. The volatile siloxanes are present as about 16–24% by weight of the formulation preferably about 18–20% by weight.

The formulation also contains 15–20% preferably about 17–18% water.

The formulation also contains about 1% fragrance and can contain a water soluble thickener such as the compound talloweth-60 myristyl glycol available under the tradename Elfacos GT 282 S. This thickener, when present, comprises about 5% of the formulation.

It is apparent that the formulation does not contain anionic gelling agents or sodium or magnesium soaps. No neutralization occurs, and the active ingredient remain compatable and and thus more effective. Emolliency and detapification is imparted to the formulation by the addition of the volatile silicone compositions. These polydimethylsiloxanes have the structural formula $[(CH_3)_2 SiO]_x$ where x is interger of about 4-6. The nonvolitile emollient ingredient in the formulation reduces the whiting action of the cyclomethicones.

The formulation is prepared in three phases. In a typical preparation water in the amount equal to 17.5% by weight of the formulation mixed with aluminumchlorhydrate (Wickenol CPS 331) in an amount equal 24% by weight of the final formulation. Phase two of the formulation is prepared by mixing the PPG-10 cetylether, in an amount equal to about 4% by weight of the formulation with PPG-5 ceteth-20 in an amount equal to about 10% by weight of the formulation and with the Dow Corning Silicone 244 in an amount equal 19% by weight of the formulation and Dow Corning Silicone 556 in the amount equal to 1% by weight of the formulation the isostearylbenzoate is added as Finsolv SB in the amount equal to about 19.5% by weight of the formulation. The third phase is glycerine USP in the present amount about 4% of formulation and fragrance about 1% formulation.

These phases are mixed together to form the antipersirant gel.

The invention is illustrated by the following specific but non-limiting examples.

EXAMPLE I

TABLE I

| Formulation | 1 | 2 | 3 |
|---|---|---|---|
| Water | 18.0 | 18.0 | 17.5 |
| Wickenol CPS331 | 24.0 | 24.0 | 24.0 |
| PPG-10 CETYLETHER | 4.0 | 4.0 | 4.0 |
| PPG-5 Ceteth-20 | 10 | 10.0 | 10.0 |
| Silicone 244 | — | 20.0 | — |
| Silicone 344 | 20.0 | — | 20.0 |
| Silicone 556 | — | — | 1.0 |
| Finsolv SB | 19.0 | 19.0 | 19.0 |
| Glycerin | 4.0 | 4.0 | 4.0 |
| Frag. | 1.0 | 1.0 | Q.S |

The formulations are essentially the same except for the silicone. Silicone 244 found to give gel that are more more rigid than the gels prepared with Silicone 344.

Each of the formulations set out above gave very good results, all three are very stable Formulation 1 gave the best results in the panel test. In the panel test samples of each product were sent out to a total of 40 teenage girls with instructions to use the product for 3 days and to report their findings by answering questions posed in a questionaire.

EXAMPLE II

Additional formulations were prepared and gave good results. The formulations are set out in Table II below:

TABLE II

| Formulation | 1 | 2 | 3 |
|---|---|---|---|
| Water | 20.0 | 20.0 | 20.0 |
| Wickenol SPS 331 | 26.0 | 22.0 | 26.0 |
| PPG-10 CETYLETHER | 4.0 | 4.0 | 4.0 |
| PPG-5 CETETH-20 | 10.0 | 10.0 | 11.0 |
| SILICONE 244 | 20.0 | 20.0 | 22.0 |
| Finsolv SB | 16.0 | 16.0 | 13.5 |
| GLYCERIN | 3.5 | 3.5 | 3.0 |
| ARLAMOL E | — | 4.0 | — |
| Fragrance | Q.S | Q.S | Q.S |

The formulation designated 1 were very clear. The formulation designated 2 gave very good results but it had a slight haze. The formulation designated 3 was good firm gel. Increasing the amount of aluminumchlorhydrate and adding the volatile emollient Arlamol E in formulation 2 formulated a good clear gel with a slight haze.

EXAMPLE III

In addition to the formulations as prepared in which the aluminumchlorhydrate was a mixture of Wickenol and the aluminumchlorhydrate designated Germal II by the bender. Carbowax was added to each of these formulations. The results are set out in Table III.

TABLE III

| Formulation | 1 | 2 | 3 | 4 |
|---|---|---|---|---|
| Water | 18.0 | 18.0 | 18.0 | 18.0 |
| Wickenol CPS 331 | 18.0 | 18.0 | 18.0 | 18.0 |
| Germall II | | | | 0.5 |
| PPG-10 CETYLETHER | 5.4 | 5.0 | 5.0 | 5.0 |
| PPG-5 CETETH-2 | 19.5 | 20.0 | 15.0 | 20.0 |
| DOW SILICONE 334 | — | — | 23.0 | — |
| DOW SILICONE 244 | 14.0 | 18.0 | — | 18.0 |
| Isostearyl Benzoate | | | | |
| Finsolv SB | 14.5 | 14.0 | 14.0 | 13.0 |
| PEG-400 CARBOWAX | 5.0 | 7.0 | 7.0 | 7.0 |
| PPG-4000 | 4.8 | — | — | — |
| Fragrance | — | — | — | — |

These formulations show the effect of substituting Carbowax for the glycerin or propyleneglycol solubilizers. Formulation 1 was a translucent gel, Formulation 2 was a very clear gel It was stable but the physical properties of the gel were not particularly satisfactory, Formulation 3 was a clear stable gel that dried quickly. Formulation 4 was a clear stable gel and had the best overall properties of this group of formulations. You will note that formulation 4 contains 0.50, weight percent Germal II as well as the Wickenol CPS 331.

Methods of preparing the formulation is set out in Example IV below.

EXAMPLE IV

Phase I of the formulation was prepared by dissolving 24 grams of the aluminchlorohydrate superfine powder (85% below 10 micron particle size) designated Wickenol CPS 331 in 18 ml of water The mixture was heated to 60°-65° C. for about 45 minutes to accelerate dissolution.

Phase II of the formulation was prepared by mixing 4 grams of cetylether, (PPG 5) 10 grams of cetylether (PPG 5) ceteth 20, 20+1 grams of silicone fluids (Dow Corning 244 and 556) 19 grams of isostearylbenzoate (Finsolv SB) at room temperature until a clear solution formed.

Phases III and IV were prepared by separately weighing 4 grams of glycerine and 1 grams of fragrance. The phases were combined by heating the phase II components to 45°-50° C. with thorough mixing. The phase I component was heated to 50°-60° C. and added to the phase II component over a period of 30 minutes. A thixotropic mixture formed after about 10 to 15 minutes. The addition of the phase I component was discontinued and stirring was continued until the thixotropic mixture broke down to a viscous solution. At this point the remainder of the phase I component was slowly added. The agitator speed was increased. The addition was continued until a clear homogeneous gel started to form. The mixing was continued for 10 minutes. The phase III component was heated to 60°-65° C. and added over a period of 5 minutes. The batch was allowed to cool to about 30° to 35 ° C. and the phase IV component was added while the formulation was stirred. The formulation was packaged at a temperature of about 30°-35° C.

Obviously many modifications of the invention have been made but particle in the essence of thereof such limitations should be applied as indicated in the pending claims.

What is claimed is:

1. A clear, quick drying highly active antiperspirant and deodorant gel, free of monohydric alcohols which comprises in combination
   (a) from about 18 to 26% by weight aluminum chlorohydrate,
   (b) from about 15 to 29% by weight water,
   (c) from about 13 to 20% by weight isostearyl benzoate emollient,
   (d) from about 10 to 20% by weight volatile siloxanes,
   (e) from about 14 to 25% by weight cetyl ether emollient,
   (f) from about 2 to 6% by weight glycol solubilizers.

2. The antiperspirant and deodorant gel according to claim 1 wherein the volatile siloxanes are cyclic siloxanes composed of low molecular weight polydimethycyclosiloxanes having the structural formula $$[CH_3)_2SiO]_x$$

wherein X is an integer from 4 to 6.

3. A clear, quick drying highly active antiperspirant and deodorant gel, free of monohydric alcohols having 2-8 carbon atoms in the molecule which consists essentially of:
   (a) from about 18 to 26% by weight aluminum chlorohydrate,
   (b) from about 15 to 20% by weight water,
   (c) from about 13 to 15% by weight isostearyl benzoate,
   (d) from about 20 to 25% by weight cetyl ether,
   (e) from about 18 to 20% by weight polydimethylcyclosiloxanes,
   (f) from about 3 to 5 ) by weight glycerine and
   (g) about 1% fragrance.

4. The antiperspirant and deodorant gel of claim 1 consisting of:
   (a) about 24% by weight aluminum chlorohydrate,
   (b) 17.5 to 18% by weight water,
   (c) about 14% by weight cetyl ether,
   (d) about 21A% by weight low molecular weight polydimethycyclosiloxanes,
   (e) about 19% by weight isostearyl benzoate,
   (f) about 4% by weight glycerine, and
   (g) about 1% by weight fragrance.

* * * * *